US008696926B2

(12) United States Patent
Rao et al.

(10) Patent No.: US 8,696,926 B2
(45) Date of Patent: *Apr. 15, 2014

(54) PROCESSES FOR THE PRODUCTION OF FLUOROPROPANES AND HALOPROPENES AND AZEOTROPIC COMPOSITIONS OF 2-CHLORO-3,3,3-TRIFLUORO-1-PROPENE WITH HF AND OF 1,1,1,2,2-PENTAFLUOROPROPANE WITH HF

(71) Applicant: E I du Pont de Nemours and Company, Wilmington, DE (US)

(72) Inventors: Velliyur Nott Mallikarjuna Rao, Wilmington, DE (US); Allen Capron Sievert, Elkton, MD (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/688,720

(22) Filed: Nov. 29, 2012

(65) Prior Publication Data
US 2013/0102814 A1 Apr. 25, 2013

Related U.S. Application Data

(62) Division of application No. 12/444,470, filed as application No. PCT/US2007/022994 on Oct. 31, 2007, now Pat. No. 8,398,882.

(60) Provisional application No. 60/855,540, filed on Oct. 31, 2006.

(51) Int. Cl.
C09K 5/04 (2006.01)
C07C 21/18 (2006.01)

(52) U.S. Cl.
USPC .............. 252/67; 570/136; 570/134; 570/160

(58) Field of Classification Search
USPC ............................. 252/67; 570/136, 134, 160
See application file for complete search history.

(56) References Cited

U.S. PATENT DOCUMENTS

| 2,787,646 | A | 4/1957 | Haszeldine |
| 2,996,555 | A | 8/1961 | Rausch |
| 4,650,914 | A | 3/1987 | Woodard |
| 5,057,634 | A | 10/1991 | Webster et al. |
| 5,177,273 | A | 1/1993 | Bruhnke et al. |
| 5,396,000 | A | 3/1995 | Nappa et al. |
| 5,788,886 | A | 8/1998 | Minor et al. |
| 5,895,825 | A | 4/1999 | Elsheikh et al. |
| 6,013,846 | A | 1/2000 | Wismer et al. |
| 6,111,150 | A | 8/2000 | Sakyu et al. |
| 6,124,510 | A | 9/2000 | Elsheikh et al. |
| 6,184,426 | B1 | 2/2001 | Belen'Kill et al. |
| 6,224,781 | B1 | 5/2001 | Mahler et al. |
| 6,291,730 | B1 | 9/2001 | Baker et al. |
| 6,329,559 | B1 | 12/2001 | Sievert et al. |
| 6,540,933 | B1 * | 4/2003 | Sievert et al. ............... 252/67 |
| 7,217,678 | B2 * | 5/2007 | Rao et al. ................. 502/224 |
| 7,423,188 | B2 * | 9/2008 | Miller et al. .............. 570/155 |
| 7,678,949 | B2 * | 3/2010 | Rao et al. ................. 570/156 |
| 7,722,781 | B2 * | 5/2010 | Rao et al. .................... 252/67 |
| 7,872,161 | B2 * | 1/2011 | Rao et al. ................. 570/176 |
| 7,982,073 | B2 * | 7/2011 | Nappa et al. ............. 570/156 |
| 8,398,882 | B2 * | 3/2013 | Rao et al. .................... 252/67 |
| 2004/0167366 | A1 * | 8/2004 | Rao et al. ................. 570/177 |
| 2004/0236161 | A1 * | 11/2004 | Rao et al. ................. 570/177 |
| 2005/0228202 | A1 * | 10/2005 | Nappa et al. ............. 570/161 |
| 2005/0245773 | A1 | 11/2005 | Mukhopadhyay et al. |
| 2006/0030744 | A1 * | 2/2006 | Mukhopadhyay et al. ... 570/164 |
| 2006/0094911 | A1 * | 5/2006 | Rao et al. ................. 570/155 |
| 2006/0106263 | A1 * | 5/2006 | Miller et al. .............. 570/155 |
| 2006/0217577 | A1 * | 9/2006 | Mukhopadhyay et al. ... 570/156 |
| 2006/0217578 | A1 * | 9/2006 | Rao et al. ................. 570/165 |
| 2007/0100175 | A1 * | 5/2007 | Miller et al. .............. 570/178 |
| 2007/0123742 | A1 * | 5/2007 | Rao et al. ................. 570/161 |
| 2008/0207962 | A1 * | 8/2008 | Rao et al. ................. 570/156 |
| 2008/0207963 | A1 * | 8/2008 | Rao et al. ................. 570/156 |
| 2008/0207964 | A1 * | 8/2008 | Rao et al. ................. 570/169 |
| 2009/0043137 | A1 * | 2/2009 | Wang et al. ............... 570/136 |
| 2009/0043138 | A1 * | 2/2009 | Rao et al. ................. 570/156 |

(Continued)

FOREIGN PATENT DOCUMENTS

JP 49066613 6/1974
JP 10309464 11/1998

(Continued)

OTHER PUBLICATIONS

Heterogeneous Catalysis in Industrial Practice, 2nd Edition (McGraw-Hill, New York, 1991), Author: Satterfield, pp. 87-112.
Haszeldine—Journal of Chemical Society (1951), pp. 2495-2504.
Ind. Eng. Chem. Process Des. Dev. (1980) 19, Author: W. Schotte, pp. 432-439.
CAS Reg. No. 1814-88-6, Nov. 16, 1984.
CAS Reg. No. 754-12-1, Nov. 16, 1984.
CAS Reg. No. 2730-62-3, Nov. 16, 1984.

(Continued)

Primary Examiner — Douglas Mc Ginty

(57) ABSTRACT

A process is disclosed for making $CF_3CH_2CHF_2$, $CF_3CH=CHF$ and/or $CF_3CH=CHCl$. The process involves reacting at least one starting material selected from the group consisting of halopropanes of the formula $CX_3CHClCH_2X$, halopropenes of the formula $CX_3CCl=CH_2$ and halopropenes of the formula $CX_2=CClCH_2X$, wherein each X is independently F or Cl, with HF in a reaction zone to produce a product mixture comprising HF, HCl, $CF_3CH_2CHF_2$, $CF_3CH=CHF$ and $CF_3CH=CHCl$; and recovering the $CF_3CH_2CHF_2$, $CF_3CH=CHF$ and/or $CF_3CH=CHCl$ from the product mixture. Also disclosed is a process for making $CF_3CF_2CH_3$ and/or $CF_3CF=CH_2$. In each of the processes the molar ratio of HF to total amount of starting material fed to the reaction zone is at least stoichiometric. Also disclosed is an azeotropic composition comprising $CF_3CCl=CH_2$, and HF. Also disclosed is an azeotropic composition comprising $CF_3CF_2CH_3$, and HF.

9 Claims, No Drawings

(56) References Cited

U.S. PATENT DOCUMENTS

| | | |
|---|---|---|
| 2009/0118554 A1 | 5/2009 | Rao et al. |
| 2009/0127496 A1 | 5/2009 | Rao et al. |
| 2009/0264689 A1 | 10/2009 | Rao et al. |
| 2010/0004492 A1 | 1/2010 | Nappa et al. |
| 2010/0025620 A1 | 2/2010 | Nappa et al. |
| 2010/0051852 A1 | 3/2010 | Rao et al. |
| 2010/0051853 A1 | 3/2010 | Rao et al. |
| 2010/0076231 A1 | 3/2010 | Nappa et al. |
| 2010/0168482 A1 | 7/2010 | Rao et al. |
| 2010/0200798 A1* | 8/2010 | Rao et al. ......... 252/67 |
| 2010/0320412 A1 | 12/2010 | Nappa et al. |

FOREIGN PATENT DOCUMENTS

| | | | |
|---|---|---|---|
| WO | 97/05089 | 2/1997 | |
| WO | 98/42645 | 10/1998 | |
| WO | WO 2007019355 A1 * | 2/2007 | ............ C07C 17/21 |
| WO | WO 2007019358 A2 * | 2/2007 | ............ B01J 23/86 |
| WO | WO 2008002499 A2 * | 1/2008 | ............ C07C 21/18 |
| WO | 2008/054782 A1 | 5/2008 | |

\* cited by examiner

PROCESSES FOR THE PRODUCTION OF FLUOROPROPANES AND HALOPROPENES AND AZEOTROPIC COMPOSITIONS OF 2-CHLORO-3,3,3-TRIFLUORO-1-PROPENE WITH HF AND OF 1,1,1,2,2-PENTAFLUOROPROPANE WITH HF

CROSS-REFERENCE TO RELATED APPLICATION

This application is a division of application Ser. No. 12/444,470 filed Apr. 6, 2009 now U.S. Pat. No. 8,398,882, which represents a national filing under 35 U.S.C. 371 of International Application No. PCT/US2007/022994 filed Oct. 31, 2007, and claims priority of U.S. Provisional Application No. 60/855,540 filed Oct. 31, 2006.

FIELD OF THE INVENTION

The present invention relates to processes for the production of 1,1,1,2,2-pentafluoropropane, 2,3,3,3-tetrafluoro-1-propene, 1,1,1,3,3-pentafluoropropane, 1,3,3,3-tetrafluoro-1-propene, 2-chloro-3,3,3-trifluoro-1-propene and/or 1-chloro-3,3,3-trifluoro-1-propene.

BACKGROUND OF THE INVENTION

As a result of the Montreal Protocol phasing out ozone depleting chlorofluorocarbons (CFCs) and hydrochlorofluorocarbons (HCFCs), industry has been working for the past few decades to find replacement refrigerants. The solution for most refrigerant producers has been the commercialization of hydrofluorocarbon (HFC) refrigerants. The new hydrofluorocarbon refrigerants, HFC-134a being the most widely used at this time, have zero ozone depletion potential and thus are not affected by the current regulatory phase out as a result of the Montreal Protocol. The production of other hydrofluorocarbons for use in applications such as solvents, blowing agents, cleaning agents, aerosol propellants, heat transfer media, dielectrics, fire extinguishants and power cycle working fluids has also been the subject of considerable interest.

There is also considerable interest in developing new refrigerants with reduced global warming potential for the mobile air-conditioning market.

1,1,1,3,3-Pentafluoropropane ($CF_3CH_2CHF_2$ or HFC-245fa), a refrigerant and blowing agent, may be prepared by fluorination of 1,1,1,3,3-pentachloropropane ($CCl_3CH_2CHCl_2$ or HCC-240fa) in the liquid phase (see for example, U.S. Pat. No. 6,291,730).

1,1,1,2,2-Pentapropane ($CF_3CF_2CH_3$ or HFC-245cb), useful as a refrigerant and blowing agent has been prepared by the addition of methyl fluoride to tetrafluoroethylene in the presence of antimony pentafluoride as disclosed in U.S. Pat. No. 6,184,426.

2,3,3,3-Tetrafluoro-1-propene ($CF_3CF=CH_2$ or HFC-1234yf), useful as a refrigerant and as a polymer intermediate has been prepared by fluorination of $CH_3CF_2CCl_3$ over chromium oxide as disclosed by Rausch in U.S. Pat. No. 2,996,555.

1-Chloro-3,3,3-trifluoro-1-propene ($CF_3CH=CHCl$ or HCFC-1233zd) is useful as a chemical intermediate and may be prepared by fluorination of HCC-240fa as disclosed in U.S. Pat. No. 6,013,846.

1,3,3,3-Tetrafluoro-1-propene ($CF_3CH=CHF$ or HFC-1234ze) useful as a refrigerant has been prepared by dehydrofluorination of HFC-245fa using a strong base in aqueous or alcoholic solution or by means of chromium-containing catalyst in the presence of oxygen at elevated temperature as disclosed in U.S. Pat. No. 6,124,510, and from HCFC-1233zd as disclosed in U.S. Pat. No. 5,895,825. HFC-1234ze has also been prepared from HCC-240fa as disclosed in U.S. Pat. No. 6,111,150.

2-Chloro-3,3,3-trifluoro-1-propene ($CF_3CCl=CH_2$ or HCFC-1233xf) is useful as an intermediate and as a monomer for polymers. HCFC-1233xf has been prepared by dehydrochlorination of 1,2-dichloro-3,3,3-trifluoropropane using potassium hydroxide as described by Haszeldine in Journal of the Chemical Society (1951) pages 2495 to 2504.

There is a need for processes for the manufacture of a compound from the group HCFC-1233xf, HFC-245fa, HFC-245cb, HFC-1234ze, HCFC-1233zd, and HFC-1234yf, where other compounds of the group are also produced from common halogenated hydrocarbon starting materials and those other compounds can, if desired, also be recovered.

SUMMARY OF THE INVENTION

The present invention provides a process for making at least one product compound selected from the group consisting of $CF_3CF_2CH_3$, $CF_3CF=CH_2$ and $CF_3CCl=CH_2$. The process comprises reacting at least one starting material selected from the group consisting of halopropanes of the formula $CX_3CHClCH_2X$, halopropenes of the formula $CClX_2CCl=CH_2$ and halopropenes of the formula $CX_2=CClCH_2X$, wherein each X is independently selected from the group consisting of F and Cl, with HF in a reaction zone, optionally in the presence of a fluorination catalyst, to produce a product mixture comprising HF, HCl, $CF_3CF_2CH_3$, $CF_3CF=CH_2$ and $CF_3CCl=CH_2$, wherein the molar ratio of HF to total amount of starting material fed to the reaction zone is at least stoichiometric; and recovering said at least one product compound from the product mixture.

The present invention also provides a process for making at least one product compound selected from the group consisting of $CF_3CH_2CHF_2$, $CF_3CH=CHF$ and $CF_3CH=CHCl$. The process comprises reacting at least one starting material selected from the group consisting of halopropanes of the formula $CX_3CHClCH_2X$, halopropenes of the formula $CX_3CCl=CH_2$ and halopropenes of the formula $CX_2=CClCH_2X$, wherein each X is independently selected from the group consisting of F and Cl, with HF in a reaction zone, optionally in the presence of a fluorination catalyst, to produce a product mixture comprising HF, HCl, $CF_3CH_2CHF_2$, $CF_3CH=CHF$ and $CF_3CH=CHCl$, wherein the molar ratio of HF to total amount of starting material fed to the reaction zone is at least stoichiometric; and recovering said at least one product compound from the product mixture.

The present invention also provides a process for making at least one product compound selected from the group consisting of $CF_3CF_2CH_3$ and $CF_3CF=CH_2$. The process comprises reacting at least one starting material selected from the group consisting of halopropanes of the formula $CX_3CHClCH_2X$, halopropenes of the formula $CX_3CCl=CH_2$ and halopropenes of the formula $CX_2=CClCH_2X$, wherein each X is independently selected from the group consisting of F and Cl, with HF in a reaction zone, optionally in the presence of a fluorination catalyst, to produce a product mixture comprising HF, HCl, $CF_3CF_2CH_3$ and $CF_3CF=CH_2$, wherein the molar ratio of HF to total amount of starting material fed to the reaction zone is at least stoichiometric; and recovering said at least one product compound from the product mixture.

The present invention also provides azeotropic compositions. A composition is provided that comprises $CF_3CCl=CH_2$ and HF; wherein the HF is present in an effective amount to form an azeotropic combination with the $CF_3CCl=CH_2$. Another composition is provided that comprises $CF_3CF_2CH_3$ and HF; wherein the HF is present in an effective amount to form an azeotropic combination with the $CF_3CF_2CH_3$.

DETAILED DESCRIPTION

The term "starting material", as used herein, means halopropanes or halopropenes which react with hydrogen fluoride (HF) in a reaction zone in the embodiments of this invention. As indicated above, for certain processes of this invention, the starting material is selected from the group consisting of halopropanes of the formula $CX_3CHClCH_2X$, halopropenes of the formula $CClX_2CCl=CH_2$ and halopropenes of the formula $CX_2=CClCH_2X$, wherein each X is independently selected from the group consisting of F and Cl; and for certain other processes of this invention, the starting material is selected from the group consisting of halopropanes of the formula $CX_3CHClCH_2X$, halopropenes of the formula $CX_3CCl=CH_2$ and halopropenes of the formula $CX_2=CClCH_2X$, wherein each X is independently selected from the group consisting of F and Cl.

The processes of this invention use a molar ratio of HF to the total amount of starting material that is at least stoichiometric. The stoichiometric ratio is determined by subtracting the weighted average of the number of fluorine substituents in the starting material(s) from the weighted average of the number of fluorine substituents in the desired product(s). For example, for producing a $C_3H_3F_5$ isomer from $C_3H_3Cl_5$, the stoichiometric ratio of HF to $C_3H_3Cl_5$ is 5:1. As another example, for producing a 1:1 mixture of HFC-245cb to HFC-1234yf from $CF_3CCl=CH_2$, the stoichiometric ratio of HF to $CF_3CCl=CH_2$ is 1.5:1.

Certain compounds produced by the processes of this invention may exist as one of two configurational isomers. For example, HFC-1234ze and HCFC-1233zd may each exist as E- or Z-isomers. As used herein HFC-1234ze refers to the isomers, E-HFC-1234ze or Z-HFC-1234ze, as well as any combinations or mixtures of such isomers; and HCFC-1233zd as used herein refers to the isomers, E-HCFC-1233zd or Z-HCFC-1233zd, as well as any combinations or mixtures of such isomers.

As indicated above, the present invention provides a process that involves producing a product mixture comprising at least one product compound selected from the group consisting of HFC-245cb, HFC-1234yf and HCFC-1233xf using at least one starting material selected from the group consisting of halopropanes of the formula $CX_3CHClCH_2X$, halopropenes of the formula $CClX_2CCl=CH_2$ and halopropenes of the formula $CX_2=CClCH_2X$. Of note are embodiments of this process wherein HFC-1234yf is recovered. Additional HFC-1234yf may be obtained by dehydrofluorination of HFC-245cb from the product mixture. Also of note are embodiments of this process wherein HCFC-1233xf from the product mixture is fluorinated to produce at least one of HFC-1234yf and HFC-245cb.

The product mixture may also comprise HFC-1234ze. The HFC-1234ze may be recovered. The product mixture may further comprise HCFC-1233zd. HFC-1234ze and HFC-245fa may also be obtained by fluorination of HCFC-1233zd from the product mixture.

The product mixture may also comprise HFC-245fa. The HFC-245fa may be recovered. The HFC-245fa may also be dehydrofluorinated to produce HFC-1234ze.

The product mixture may further comprise HFC-1234ze. A mixture of HFC-245cb and HFC-1234ze may be recovered and further reacted with HF in the liquid phase under fluorination conditions in the presence of a fluorination catalyst to produce a mixture comprising HFC-245fa and HFC-245cb. Alternatively, a mixture of HFC-245cb and HFC-1234ze may be recovered and further reacted under dehydrofluorination conditions in the presence of a dehydrofluorination catalyst to produce a mixture comprising HFC-1234ze and HFC-1234yf.

HFC-245fa, HFC-1234ze and/or HCFC-1233zd may also be present in the product mixture. HFC-245cb, HFC-1234yf and HCFC-1233xf from the product mixture together with HFC-245fa (if present), HFC-1234ze (if present) and HCFC-1233zd (if present) may be further reacted with HF in the liquid phase under fluorination conditions in the presence of a fluorination catalyst to produce a mixture comprising HFC-245fa and HFC-245cb. The HFC-245fa and HFC-245cb from the mixture may be dehydrofluorinated (individually or as a mixture) to produce both HFC-1234ze and HFC-1234yf which may be recovered. See for example, U.S. Patent Application Publication US2006/0106263(A1), which is herein incorporated by reference.

HCFC-1233zd and HFC-245fa may also be present in the product mixture; and HCFC-1233xf, HCFC-1233zd, and HFC-245fa from the product mixture may be further reacted with HF in the liquid phase under fluorination conditions in the presence of a fluorination catalyst to produce a mixture comprising $CF_3CH_2CHF_2$ and $CF_3CF_2CH_3$.

As indicated above, the present invention also provides a process that involves producing a product mixture comprising HFC-245fa, HFC-1234ze and HCFC-1233zd using at least one starting material selected from the group consisting of halopropanes of the formula $CX_3CHClCH_2X$, halopropenes of the formula $CX_3CCl=CH_2$ and halopropenes of the formula $CX_2=CClCH_2X$. Of note are embodiments of the process wherein HFC-1234ze is recovered. Additional HFC-1234ze may be obtained by dehydrofluorination of HFC-245fa from the product mixture. Also of note are embodiments of this process wherein HCFC-1233zd from the product mixture is fluorinated to produce at least one of HFC-1234ze and HFC-245fa.

Also of note are processes wherein HFC-245fa is recovered.

Also of note are processes wherein the product mixture further comprises HFC-1234yf and wherein HFC-1234yf from the product mixture is recovered.

The product mixture may further comprise HFC-245cb. A mixture of HFC-245cb and HFC-1234ze may be recovered and further reacted with HF in the liquid phase under fluorination conditions in the presence of a fluorination catalyst to produce a mixture comprising HFC-245fa and HFC-245cb. Alternatively, a mixture of HFC-245cb and HFC-1234ze may be recovered and further reacted under dehydrofluorination conditions in the presence of a dehydrofluorination catalyst to produce a mixture comprising HFC-1234ze and HFC-1234yf.

HFC-245cb, HFC-1234yf and/or HCFC-1233xf may also be present in the product mixture. HFC-245fa, HFC-1234ze and HCFC-1233zd from the product mixture together with HFC-245cb (if present), HFC-1234yf (if present) and HCFC-1233xf (if present) may be further reacted with HF in the liquid phase under fluorination conditions in the presence of a fluorination catalyst to produce a mixture comprising HFC-245fa and HFC-245cb. The HFC-245fa and HFC-245cb from the mixture may be dehydrofluorinated (individually or as a mixture) to produce both HFC-1234ze and HFC-1234yf which may be recovered. See for example, U.S. Patent Application Publication US2006/0106263(A1).

HCFC-1233xf may also be present in the product mixture; and HCFC-1233xf, HCFC-1233zd, and HFC-245fa from the product mixture may be further reacted with HF in the liquid phase under fluorination conditions in the presence of a fluorination catalyst to produce a mixture comprising $CF_3CH_2CHF_2$ and $CF_3CF_2CH_3$.

As indicated above, the present invention also provides a process that involves producing a product mixture comprising HFC-245cb and HFC-1234yf using at least one starting material selected from the group consisting of halopropanes of the formula $CX_3CHClCH_2X$, halopropenes of the formula $CX_3CCl=CH_2$ and halopropenes of the formula $CX_2=CClCH_2X$. Of note are embodiments of the process wherein HCFC-1233xf is used as a starting material.

Suitable halopropane starting materials of the formula $CX_3CHClCH_2X$ include $CCl_3CHClCH_2Cl$ (HCC-240db) and $CF_3CHClCH_2Cl$ (HCFC-243db). HCFC-243db is a readily available starting material obtained from chlorination of commercially available $CF_3CH=CH_2$ (3,3,3-trifluoro-1-propene or HFC-1243zf)

Suitable halopropene starting materials of the formula $CX_3CCl=CH_2$ include HCFC-1233xf. HCFC-1233xf can be obtained by the dehydrochlorination of HCFC-243db.

Suitable halopropene starting materials of the formula $CX_2=CClCH_2X$ include $CCl_2=CClCH_2Cl$.

The reaction may be carried out in the liquid or vapor phase. For liquid phase embodiments of the invention, the reaction of starting materials with HF may be conducted in a liquid-phase reactor operating in batch, semi-batch, semi-continuous, or continuous modes. In the batch mode, starting materials and HF are combined in an autoclave or other suitable reaction vessel and heated to the desired temperature.

Preferably, this reaction is carried out in semi-batch mode by feeding HF to a liquid-phase reactor containing starting materials or by feeding starting materials to a liquid-phase reactor containing HF, or by feeding HF to a mixture containing HF and reaction products formed by initially heating starting materials and HF. Alternatively, HF may be fed to a liquid-phase reactor containing a mixture of starting materials and reaction products formed by the reaction of HF, and starting materials. In another embodiment of the liquid-phase process, HF, and starting materials may be fed concurrently in the desired stoichiometric ratio to the reactor containing a mixture of HF and reaction products formed by reacting HF, and starting materials.

Suitable temperatures for the reaction of HF with starting materials in the liquid-phase reactor are from about 80° C. to about 180° C., preferably from about 100° C. to about 150° C. Higher temperatures typically result in greater conversion of the starting materials.

A suitable molar ratio of HF to total amount of starting materials fed to the liquid-phase reactor is at least stoichiometric and is typically from about 5:1 to about 100:1. Of note are embodiments wherein the molar ratio of HF to starting material is from about 8:1 to about 50:1.

The reactor pressure in the liquid-phase process is not critical and in batch reactions is usually the autogenous pressure of the system at the reaction temperature. The pressure of the system increases as hydrogen chloride is formed by replacement of chlorine substituents by fluorine in the starting materials and intermediate reaction products. In a continuous process it is possible to set the pressure of the reactor in such a way that the lower boiling products of the reaction, such as HCl, $CF_3CF=CH_2$, E/Z—$CF_3CH=CHF$, and $CF_3CF_2CH_3$, are vented from the reactor, optionally through a packed column or condenser. In this manner, higher boiling intermediates remain in the reactor and the volatile products are removed. Typical reactor pressures are from about 20 psig (239 kPa) to about 1,000 psig (6,994 kPa).

In embodiments of the invention in which the reaction is conducted using a liquid-phase process, catalysts which may be used include carbon, $AlF_3$, $BF_3$, $FeCl_{3-a}F_a$ (where a=0 to 3), $FeX_3$ supported on carbon, $SbCl_{3-a}F_a$, $AsF_3$, $MCl_{5-b}F_b$ (where b=0 to 5 and M=Sb, Nb, Ta, or Mo), and $M'Cl_{4-c}F_c$ (where c=0 to 4, and M'=Sn, Ti, Zr, or Hf). Preferred catalysts for the liquid phase process are $MCl_{5-b}F_b$ (where b=0 to 5 and M=Sb, Nb, or Ta).

Preferably, the reaction of HF with starting materials is carried out in the vapor phase. Typically a heated reactor is used. A number of reactor configurations are possible including horizontal or vertical orientation of the reactor as well as the sequence of reaction of the starting materials with HF. In one embodiment of the invention, the starting materials may be initially vaporized and fed to the reactor as gases.

In another embodiment of the invention, the starting materials may be contacted with HF in a pre-reactor prior to reaction in the vapor-phase reactor. The pre-reactor may be empty, but is preferably filled with a suitable packing such as Monel™ or Hastelloy™ nickel alloy turnings or wool, or other material inert to HCl and HF which allows efficient mixing of starting materials and HF vapor.

Suitable temperatures for the pre-reactor for this embodiment of the invention are from about 80° C. to about 250° C., preferably from about 100° C. to about 200° C. Temperatures greater than about 100° C. result in some conversion of the starting materials to compounds having a higher degree of fluorination. Higher temperatures result in greater conversion of the starting materials entering the reactor and a greater degree of fluorination in the converted compounds. Under these conditions, for example, a mixture of HF and HCFC-243db is converted to a mixture containing predominantly HF, HCl, HCFC-243db, HCFC-244db ($CF_3CHClCH_2F$), and HCFC-1233xf.

The degree of fluorination reflects the number of fluorine substituents that replace chlorine substituents in the starting materials and their fluorinated products. For example, HFC-245cb represents a higher degree of fluorination than HCFC-243db and HFC-1234yf represents a higher degree of fluorination than HCFC-1233xf.

The molar ratio of HF to the total amount of starting material(s) in the pre-reactor is typically from about the stoichiometric ratio of HF to the total amount of starting material to about 50:1. Preferably, the molar ratio of HF to the total amount of starting material in the pre-reactor is from about twice the stoichiometric ratio of HF to the total amount of starting material to about 30:1. In one embodiment of the invention, the preferred molar ratio of HF to the total amount of starting materials is present in the pre-reactor, and no additional amount of HF is added to the vapor-phase reaction zone.

In a preferred embodiment of the invention, the starting materials and HF are vaporized and fed to a pre-reactor or to a vapor-phase reactor.

Suitable temperatures for the vapor-phase reaction of this invention are from about 120° C. to about 500° C. Temperatures in the range of from about 300° C. to about 350° C. favor the formation of HFC-1234yf and HFC-245cb and HCFC-1233xf. Temperatures in the range of from about 350° C. to about 450° C. favor the additional formation of HFC-1234ze, HFC-245fa, and HCFC-1233zd. Higher temperatures result in greater conversion of starting materials and greater degrees of fluorination in the converted products. If the starting material is the halopropane, reactor temperatures of from about 150° C. to about 275° C. favor the formation of HCFC-1233xf as the major product.

Suitable reactor pressures for the vapor-phase reactor may be from about 1 to about 30 atmospheres. A pressure of about 15 to about 25 atmospheres may be advantageously employed to facilitate separation of HCl from other reaction products, and the suitable reaction time may vary from about 1 to about 120 seconds, preferably from about 5 to about 60 seconds.

The molar ratio of HF to the total amount of starting material(s) for the vapor-phase reaction is typically from about the stoichiometric ratio of HF to the total amount of starting material to about 50:1 and preferably from about 10:1 to about 30:1.

Preferably a catalyst is used in the reaction zone for the vapor-phase reaction of HF with starting materials. Fluorination catalysts which may be used in the vapor phase reaction of the invention include carbon; graphite; alumina; fluorided alumina; aluminum fluoride; alumina supported on carbon; aluminum fluoride supported on carbon; fluorided alumina supported on carbon; magnesium fluoride supported on aluminum fluoride; metals (including elemental metals, metal oxides, metal halides, and/or other metal salts); metals supported on aluminum fluoride; metals supported on fluorided alumina; metals supported on alumina; and metals supported on carbon; mixtures of metals.

Suitable metals for use as catalysts (optionally supported on alumina, aluminum fluoride, fluorided alumina, or carbon) include chromium, iron, cobalt, nickel, ruthenium, rhodium, palladium, osmium, iridium, platinum, manganese, rhenium, scandium, yttrium, lanthanum, titanium, zirconium, and hafnium, copper, silver, gold, zinc, and/or metals having an atomic number of 58 through 71 (i.e., the lanthanide metals). Preferably when used on a support, the total metal content of the catalyst will be from about 0.1 to about 20 percent by weight based on the total weight of the catalyst; typically from about 0.1 to about 10 percent by weight based on the total weight of the catalyst.

Typical fluorination catalysts for the vapor-phase reactions in this invention include chromium-containing catalysts including chromium(III) oxide ($Cr_2O_3$); $Cr_2O_3$ with other metals such as magnesium halides or zinc halides supported on $Cr_2O_3$; chromium(III) halides supported on carbon; mixtures of chromium and magnesium (including elemental metals, metal oxides, metal halides, and/or other metal salts) optionally supported on graphite; and mixtures of chromium and other metals (including elemental metals, metal oxides, metal halides, and/or other metal salts) optionally supported on graphite, alumina, or aluminum halides such as aluminum fluoride.

Chromium-containing catalysts are well known in the art. They may be prepared by either precipitation methods or impregnation methods as generally described by Satterfield on pages 87-112 in *Heterogeneous Catalysis in Industrial Practice*, $2^{nd}$ edition (McGraw-Hill, New York, 1991).

Of note are fluorination catalysts that comprise at least one chromium-containing component selected from the group consisting of crystalline alpha-chromium oxide where from about 0.05 atom % to about 6 atom % of the chromium atoms in the alpha-chromium oxide lattice are replaced by trivalent cobalt atoms, and crystalline alpha-chromium oxide where from about 0.05 atom % to about 6 atom % of the chromium atoms in the alpha-chromium oxide lattice are replaced by trivalent cobalt atoms which has been treated with a fluorinating agent. These catalysts, including their preparation, have been disclosed in U.S. Patent Application Publication US2005/0228202 which is incorporated herein by reference in its entirety.

Optionally, the metal-containing catalysts described above can be pretreated with HF. This pretreatment can be accomplished, for example, by placing the metal-containing catalyst in a suitable container, and thereafter, passing HF over the metal-containing catalyst. In one embodiment of this invention, such container can be the reactor used to perform the fluorination reaction in this invention. Typically, the pretreatment time is from about 15 to about 300 minutes, and the pretreatment temperature is from about 200° C. to about 450° C.

In one embodiment of this invention, the product mixture comprises HFC-245cb, HFC-245fa, HFC-1234yf, HFC-1234ze, HCFC-1233zd and HCFC-1233xf.

In cases where the product mixture produced by the processes of this invention comprises (i) product compounds HFC-245cb, HFC-245fa, HFC-1234yf, HFC-1234ze, HCFC-1233zd and HCFC-1233xf, (ii) HF and HCl, (iii) by-products and (iv) unreacted starting materials, the separation steps (a) through (e) may be employed to recover the product compounds from such a product mixture.

In separation step (a), the product mixture may be delivered to a distillation column to separate HCl from the product mixture.

In separation step (b), the product mixture from separation step (a) may be delivered to one or more distillation columns to separate the azeotropic composition of HFC-1234yf and HF from the rest of the product mixture. The recovered azeotropic composition of HFC-1234yf and HF may be further separated into individual components by using procedures similar to those described in U.S. Patent Application Publication US2006/0106263(A1) that is incorporated herein by reference.

In separation step (c), the product mixture from separation step (b) may be delivered to one or more distillation columns in which HF, HFC-245cb, HFC-1234ze, HCFC-1233xf, HCFC-1233zd, and HFC-245fa are recovered from the top of the distillation column, and the higher boiling starting materials such as $CF_3CHClCH_2C_1$, $CF_3CHClCH_2F$ are removed from the bottom of the distillation column. The $CF_3CHClCH_2C_1$ and $CF_3CHClCH_2F$ may be further separated from other by-products and unreacted starting materials, e.g. by distillation, and may be recycled back to the vapor-phase fluorination reactor.

In separation step (d), the product mixture comprising HF, HFC-245cb, HFC-1234ze, HCFC-1233xf, HCFC-1233zd and HFC-245fa, which is recovered from the top of the distillation column in separation step (c), may be delivered to one or more distillation columns to recover the azeotropic composition of HFC-245cb/HF and the azeotropic composition of HFC-1234ze/HF from the top of the distillation column. The recovered HFC-245cb/HF and HFC-1234ze/HF azeotropic compositions may then be further separated into individual components by using procedures similar to those described in U.S. Patent Application Publication US2006/0106263(A1).

In yet another embodiment of the separation step (d), the product mixture comprising HF, HFC-245cb, HFC-1234ze, HCFC-1233xf, HCFC-1233zd and HFC-245fa, which is recovered from the top of the distillation column in separation step (c), may be recycled back to the reaction zone of the vapor phase fluorination reactor.

In separation step (e), the product mixture comprising HCFC-1233xf, HCFC-1233zd and HFC-245fa and any HF recovered from the bottom of the distillation column in separation step (d) may be delivered to a distillation column to separate the HCFC-1233xf, HCFC-1233zd and HFC-245fa. The HCFC-1233xf can be fluorinated to produce at least one of HFC-245cb and HFC-1234yf. The HCFC-1233zd can be fluorinated to produce at least one of HFC-245fa and HFC-1234ze.

In isolating HCFC-1233xf in separation step (e), it is observed that HCFC-1233xf forms an azeotrope with HF.

As indicated above, in certain embodiments of this invention, the mixture of HF, HFC-245cb and HFC-1234ze, made according to the process of the invention is contacted with additional HF in a liquid-phase fluorination reactor, optionally in the presence of a liquid-phase fluorination catalyst to give a mixture of HF, HFC-245cb and HFC-245fa. The mixture of HF, HFC-245cb, and HFC-245fa is then separated into the individual components by using procedures similar to those described in U.S. Patent Application Publication US2006/0106263(A1). Suitable fluorination catalysts for these embodiments may be selected from those described for the liquid-phase embodiment of the fluorination reactor described herein. The mole ratio of HF to HFC-245cb and HFC-1234ze in these embodiments is typically from about 5:1 to about 100:1, and is preferably from about 10:1 to about 40:1 based on the amount of HFC-1234ze in the mixture. Suitable temperatures for these embodiments of the invention are within the range of from about 30° C. to about 180° C., preferably from about 50° C. to about 150° C. Suitable reactor pressures for these embodiments are usually the autogenous pressures at the reactor temperatures. The pressure may be in the range of from about 1 to about 30 atmospheres.

As indicated above, in certain embodiments of this invention, a mixture of HF, HFC-245cb and HFC-1234ze, made according to the processes of this invention, may be delivered to a reaction zone containing a dehydrofluorination catalyst (optionally after removal of the HF). Conditions in the reaction zone are chosen to be suitable for conversion of HFC-245cb to HFC-1234yf. The products leaving the reactor, comprising HFC-1234ze and HFC-1234yf are separated by techniques known to the art. Catalysts suitable for these embodiments of the invention and suitable operating conditions are disclosed in U.S. Pat. No. 5,396,000 the teachings of which are herein incorporated by reference. Preferably, the dehydrofluorination catalyst comprises aluminum fluoride or fluorided alumina or trivalent chromium oxide. Reaction temperatures suitable for these embodiments are from about 150° C. to about 500° C. Contact times in the reaction zone for these embodiments are typically from about 1 second to about 500 seconds.

As indicated above, in certain embodiments of this invention, a mixture of HCFC-1233xf, HCFC-1233zd, and HFC-245fa made according to the process of the invention, is reacted with HF in a liquid-phase fluorination reactor in the presence of a liquid-phase fluorination catalyst to give a mixture of HF, HFC-245cb and HFC-245fa. The conditions of the fluorination are similar to those described for the mixture of HFC-1234ze and HFC-245cb above. The mixture of HF, HFC-245cb, and HFC-245fa is then optionally delivered to a distillation column to separate the two pentafluoropropanes and azeotropic HF by using procedures similar to those described in U.S. Patent Application Publication US2006/0106263(A1).

As noted above, HFC-245cb, made according to the processes of this invention, may be dehydrofluorinated to produce HFC-1234yf, and HFC-245fa, made according to the processes of this invention, may be dehydrofluorinated to produce HFC-1234ze. Typical dehydrofluorination reaction conditions and dehydrofluorination catalysts are disclosed in U.S. Pat. No. 5,396,000, which is herein incorporated by reference. Dehydrofluorination reaction temperatures suitable for this invention are from about 150° C. to about 500° C.; however, higher temperature are desirable for the dehydrofluorination of HFC-245cb. Suitable contact times for these dehydrofluorinations are from about 1 second to about 500 seconds. Preferably, the dehydrofluorination catalyst comprises at least one catalyst selected from the group consisting of aluminum fluoride, fluorided alumina, and trivalent chromium oxide.

As indicated above, in certain embodiments of this invention, a mixture of HFC-245cb, HFC-1234yf, HFC-1234ze, HCFC-1233xf, HCFC-1233zd, and HFC-245fa that are present in the product mixtures made according to the processes of the invention, is reacted with HF in a liquid-phase fluorination reactor in the presence of a liquid-phase fluorination catalyst. The conditions of the fluorination are similar to those described for the mixture of HFC-1234ze and HFC-245cb above. The fluorination catalysts for the above liquid-phase embodiments of the invention may be selected from those described for the liquid-phase embodiment the fluorination reactor described herein.

The amount of HF required for the liquid-phase reaction is determined by the total amount of HFC-1234yf, HFC-1234ze, HCFC-1233xf, and HCFC-1233zd, present in the mixture. The mole ratio of HF to the sum of the moles of HFC-1234yf, HFC-1234ze, HCFC-1233xf, and E/Z-HCFC-1233zd is typically from about the stoichiometric amount (between 1:1 to 2:1) to about 100:1, and is preferably from about 8:1 to about 50:1. Suitable temperatures for these embodiments of the invention are typically within the range of from about 30° C. to about 180° C., preferably from about 50° C. to about 150° C. The resulting mixture of pentafluoropropanes (i.e, HFC-245cb and HFC-245fa) may be then be freed of HF and recovered as individual compounds by techniques known to the art.

In connection with developing processes for the separation of the individual compounds produced from the fluorination reactions in this invention, it is noted that HCFC-1233xf can be present as an azeotrope with HF and that HFC-245cb can be present as an azeotrope with HF.

The present invention also provides azeotrope compositions comprising an effective amount of hydrogen fluoride combined with HCFC-1233xf. By effective amount of hydrogen fluoride is meant an amount of hydrogen fluoride, which, when combined with HCFC-1233xf, results in the formation of an azeotropic mixture.

The present invention also provides azeotrope compositions comprising an effective amount of hydrogen fluoride combined with HFC-245cb. By effective amount of hydrogen fluoride is meant an amount of hydrogen fluoride, which, when combined with HFC-245cb, results in the formation of an azeotropic mixture.

As recognized in the art, an azeotrope composition is an admixture of two or more different components which, when in liquid form under a given pressure, will boil at a substantially constant temperature, which temperature may be higher or lower than the boiling temperatures of the individual components, and which will provide a vapor composition essentially identical to the liquid composition undergoing boiling.

Accordingly, the essential features of an azeotrope composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotrope composition may change when the azeotrope composition is subjected to boiling at different pressures. Thus, an azeotrope composition may be defined in terms of the unique relationship that exists among the components or in terms of the compositional ranges of the components or in terms of exact weight percentages of each component of the composition characterized by a fixed boiling point at a specified pressure. It is also recognized in the art that various azeotrope compositions (including their boiling points at particular pressures) may be calculated (see, e.g., W. Schotte Ind. Eng. Chem. Process Des. Dev. (1980) 19, 432-439). Experimental identification of azeotrope compositions involving the same components may be used to confirm the accuracy of such calculations and/or to modify the calculations at the same or other temperatures and pressures.

In accordance with this invention, compositions are provided which comprise the HCFC-1233xf and HF, wherein the HF is present in an effective amount to form an azeotropic combination with the HCFC-1233xf. According to calculations, these compositions comprise from about 71 mole percent to about 60 mole percent HF and from about 29 mole percent to about 40 mole percent HCFC-1233xf (which form azeotropes boiling at a temperature of from between about 0° C. and about 100° C. and at a pressure of from between about 14.3 psi (98.6 kPa) and about 277 psi (1907 kPa)).

Compositions may be formed that consist essentially of azeotrope combinations of hydrogen fluoride with HCFC-1233xf. These include compositions calculated to consist essentially of from about 71 mole percent to about 60 mole percent HF and from about 29 mole percent to about 40 mole percent HCFC-1233xf (which form azeotropes boiling at a temperature of from between about 0° C. and about 100° C. and at a pressure of from between about 14.3 psi (98.6 kPa) and about 277 psi (1907 kPa)).

Subsequent to these calculations, it has been confirmed based on experiments that azeotropes of HCFC-1233xf and HF are formed at a variety of temperatures and pressures. For example, an azeotrope of HF and HCFC-1233xf at 29.84° C. and 45.8 psi (315.9 kPa) has been found to consist essentially of about 68.4 mole percent HF and about 31.6 mole percent HCFC-1233xf. An azeotrope of HF and HCFC-1233xf at 54.74° C. and 96.7 psi (666.9 kPa) has been calculated to consist essentially of about 66.6 mole percent HF and about 33.4 mole percent HCFC-1233xf. An azeotrope of HF and HCFC-1233xf at 79.67° C. and 186.2 psi (1284.1 kPa) has been calculated to consist essentially of about 63.3 mole percent HF and about 36.7 mole percent HCFC-1233xf.

According to calculations based on the experiments, azeotropic compositions are provided that comprise from about 71.7 mole percent to about 60.2 mole percent HF and from about 28.3 mole percent to about 39.8 mole percent HCFC-1233xf (which form azeotropes boiling at a temperature of from between about 0° C. and about 100° C. and at a pressure of from between about 15.1 psi (104.1 kPa) and about 306.3 psi (2112.4 kPa)). Also provided are compositions consisting essentially of from about 71.7 mole percent to about 60.2 mole percent HF and from about 28.3 mole percent to about 39.8 mole percent HCFC-1233xf (which forms an azeotrope boiling at a temperature from between about 0° C. and about 100° C. and at a pressure of from between about 15.1 psi (104.1 kPa) and about 306.3 psi (2112.4 kPa)).

Azeotropic compositions of HF and HCFC-1233xf are useful as sources of HF to fluorinate other halogenated or unsaturated compounds. Such a fluorination, for example, can be carried out in the liquid-phase using conventional antimony pentahalide catalysts known to the art or in the vapor-phase using chromium oxide catalysts also known to the art. Further, the azeotropic composition of HF and HCFC-1233xf is also useful as a recycle stream to the fluorination reactor where both the recycled HF and HCFC-1233xf components can function as reactants. For example, as shown above, HCFC-1233xf can be used as a starting material for HFC-1234yf.

In accordance with this invention, compositions are also provided which comprise the HFC-245cb and HF, wherein the HF is present in an effective amount to form an azeotropic combination with the HFC-245cb. According to calculations based on experiments, these compositions comprise from about 25.4 mole percent to about 39.5 mole percent HF and from about 74.6 mole percent to about 60.5 mole percent HFC-245cb (which form azeotropes boiling at a temperature of from between about −40° C. and about 90° C. and at a pressure of from between about 5.6 psi (38.6 kPa) and about 413.0 psi (2848.3 kPa)).

Compositions may be formed that consist essentially of azeotrope combinations of hydrogen fluoride with HFC-245cb. These include compositions consisting essentially of from about 25.4 mole percent to about 39.5 mole percent HF and from about 74.6 mole percent to about 60.5 mole percent HFC-245cb (which form azeotropes boiling at a temperature of from between about −40° C. and about 90° C. and at a pressure of from between about 5.6 psi (38.6 kPa) and about 413.0 psi (2848.3 kPa)).

It has been determined based on experiments and calculations based on experiments that azeotropes of HFC-245cb and HF are formed at a variety of temperatures and pressures. For example, an azeotrope of HF and HFC-245cb at −20° C. and 14.7 psi (101.4 kPa) has been calculated to consist essentially of about 30.2 mole percent HF and about 69.8 mole percent HFC-245cb. An azeotrope of HF and HFC-245cb at 0° C. and 33.2 psi (229.0 kPa) has been calculated to consist essentially of about 33.3 mole percent HF and about 66.7 mole percent HFC-245cb. An azeotrope of HF and HFC-245cb at 19.87° C. and 65.7 psi (453.1 kPa) has been found to consist essentially of about 36.5 mole percent HF and about 63.5 mole percent HFC-245cb. An azeotrope of HF and HFC-245cb at 40° C. and 119.4 psi (823.4 kPa) has been calculated to consist essentially of about 38.6 mole percent HF and about 61.4 mole percent HFC-245cb. An azeotrope of HF and HFC-245cb at 59.65° C. and 200.3 psi (1381.4 kPa) has been found to consist essentially of about 39.6 mole percent HF and about 60.4 mole percent HFC-245cb.

Azeotropic compositions of HF and HFC-245cb are useful as sources of HF to fluorinate other halogenated or unsaturated compounds. Such a fluorination, for example, can be carried out in the liquid-phase using conventional antimony pentahalide catalysts known to the art or in the vapor-phase using chromium oxide catalysts also known to the art. For example, contacting an azeotropic mixture of HF and HFC-245cb with acetylene, optionally in the presence of a catalyst such as carbon, will give a mixture of HFC-245cb and HFC-152a ($CH_3CHF_2$) by fluorination of acetylene. Further, the azeotropic composition of HF and HFC-245cb is also useful as a recycle stream to the fluorination reactor where the recycled HF functions as a reactant. For example, azeotropic compositions of HF and HFC-245cb may serve as a source of HF by recycling to the reaction zone of this invention followed by contacting with halopropanes of the formula $CX_3CHClCH_2X$, halopropenes of the formula $CClX_2CCl{=}CH_2$ and/or halopropenes of the formula $CX_2{=}CClCH_2X$, as defined above.

The reactor, distillation columns, and their associated feed lines, effluent lines, and associated units used in applying the process of this invention should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

Without further elaboration, it is believed that one skilled in the art can, using the description herein, utilize the present invention to its fullest extent. The following specific embodiments are, therefore, to be construed as merely illustrative, and do not constrain the remainder of the disclosure in any way whatsoever.

EXAMPLES

Preparation of 98% Chromium/2% Cobalt Catalyst

A solution of 784.30 g $Cr(NO_3)_3[9(H_2O)]$ (1.96 moles) and 11.64 g $Co(NO_3)_2[6(H_2O)]$ (0.040 mole) was prepared in 2000 mL of deionized water. The solution was treated dropwise with 950 mL of 7.4M aqueous ammonia until the pH reached about 8.5. The slurry was stirred overnight at room temperature and then evaporated to dryness in air at 110-120° C. The dried catalyst was then calcined in air at 400° C. for 24 hours prior to use.

General Procedure for Product Analysis

The following general procedure is illustrative of the method used for analyzing the products of fluorination reactions. Part of the total reactor effluent was sampled on-line for organic product analysis using a gas chromatograph equipped a mass selective detector (GC/MS). The gas chromatography utilized a 20 ft. (6.1 m) long×⅛ in. (0.32 cm) diameter tube containing Krytox® perfluorinated polyether on an inert carbon support. The helium flow was 30 mL/min ($5.0\times10^{-7}$ m³/sec). Gas chromatographic conditions were 60° C. for an initial hold period of three minutes followed by temperature programming to 200° C. at a rate of 6° C./minute.

| LEGEND | |
|---|---|
| 243db is $CF_3CHClCH_2Cl$ | 244db is $CF_3CHClCH_2F$ |
| 245cb is $CF_3CF_2CH_3$ | 245fa is $CF_3CH_2CHF_2$ |
| 1234yf is $CF_3CF=CH_2$ | 1233xf is $CF_3CCl=CH_2$ |
| 1233zd is E— and Z—$CHCl=CHCF_3$ | 1234ze is E— and Z—$CHF=CHCF_3$ |
| 1243zf is $CH_2=CHCF_3$ | |

Examples 1-5

Fluorination of $CF_3CHClCH_2Cl$

The 98% chromium/2% cobalt catalyst prepared above (21.4 g, 15 mL, −12 to +20 mesh, (1.68 to 0.84 mm)) was placed in a ⅝" (1.58 cm) diameter Inconel™ nickel alloy reactor tube heated in a fluidized sand bath. The catalyst was pre-fluorinated by treatment with HF as follows. The catalyst was heated from 45° C. to 175° C. in a flow of nitrogen (50 cc/min) over the course of about 1.5 h. HF was then admitted to the reactor at a flow rate of 50 cc/min for 1.3 h at a temperature of 175° C. The reactor nitrogen flow was decreased to 20 cc/min and the HF flow increased to 80 cc/min; this flow was maintained for 0.3 h. The reactor temperature was then gradually increased to 400° C. over 1 h. After this period, the HF and nitrogen flow was stopped and the reactor brought to the desired operating temperature. A flow of HF vapor and $CF_3CHClCH_2Cl$ was then started through the reactor. Part of the reactor effluent was analyzed by on line GC/MS.

The results of the fluorination of $CF_3CHClCH_2Cl$ over the 98/2 Cr/Co catalyst at various operating temperatures and indicated molar ratios of HF and $CF_3CHClCH_2Cl$ are shown in Table 1; analytical data is given in units of GC area %. The nominal catalyst bed volume was 15 cc; the contact time (CT) was 15 seconds. Example 1 was carried out in the absence of the catalyst.

TABLE 1

Fluorination of HCFC-243db

| Example No. | HF/243 Ratio | Temp. (° C.) | 1243zf | 243db | 244db | 1234yf | 245cb | 1233xf | 1233zd | 1234ze | 245fa |
|---|---|---|---|---|---|---|---|---|---|---|---|
| 1 | 5/1 | 140 | 0.1 | 88.4 | 7.4 | 0 | 0 | 3.9 | 0 | 0 | 0 |
| 2 | 10/1 | 275 | 0 | 0.2 | 0.6 | 1.3 | 4.8 | 90.0 | 0 | 0.7 | 1.0 |
| 3 | 20/1 | 325 | 0 | 0 | 0 | 19.1 | 11.4 | 61.7 | 2.3 | 3.1 | 1.9 |
| 4 | 20/1 | 350 | 0 | 0 | 0 | 32.2 | 8.1 | 45.3 | 4.7 | 7.9 | 0.9 |
| 5 | 20/1 | 400 | 0 | 0 | 0 | 17.9 | 6.6 | 36.3 | 19.7 | 14.4 | 3.6 |

Example 6

Reaction of $CF_3CHClCH_2Cl$ with HF in the Presence of $TaF_5$

A 210 mL Hastelloy™ C tube was charged with 10.0 g (0.0599 mole) of HCFC-243db and 25.4 g (0.040 mole) of tantalum pentafluoride. The tube was then charged with 40.0 g (2.0 moles) of hydrogen fluoride. The tube was warmed to 150° C. and held at 149° C. to 150° C. for eight hours with shaking. The tube was then cooled to room temperature and treated with 100 mL of water. The contents of the tube were discharged and a small organic layer was collected and neutralized. The sample was 91.1% unconverted HCFC-243db; the GC-MS analysis of the converted products were as follows:

| Component | GC Area % |
|---|---|
| $CF_3CF_2CH_3$ | 39.3 |
| $CF_3CH_2CHF_2$ | 5.5 |
| $C_3H_3ClF_4$ | 9.2 |
| $C_3H_3ClF_4$ | 27.6 |
| $CF_3CH_2CH_2Cl$ | 2.9 |
| $CF_3CCl_2CH_2F$ | 8.6 |
| $CF_3CH_2CHCl_2$ | 6.9 |

The invention claimed is:

1. A process for making $CF_3CH=CHF$, comprising:
   reacting at least one starting material selected from the group consisting of halopropanes of the formula $CX_3CHClCH_2X$, halopropenes of the formula $CX_3CCl=CH_2$, and halopropenes of the formula $CX_2=CClCH_2X$, wherein each X is independently selected from the group consisting of F and Cl, with HF in a reaction zone, optionally in the presence of a fluorination catalyst, to produce a product mixture comprising $CF_3CH=CHF$, wherein the molar ratio of HF to total amount of starting material fed to the reaction zone is at least stoichiometric; and recovering said at least one product compound from the product mixture.

2. The process of claim 1 wherein $CF_3CH=CHF$ is recovered.

3. The process of claim 2 wherein said product mixture further comprises $CF_3CH_2CHF_2$ which is dehydrofluorinated to produce additional $CF_3CH=CHF$.

4. The process of claim 1 wherein said product mixture further comprises $CF_3CH=CHCl$ which is fluorinated to produce at least one of $CF_3CH_2CHF_2$ and $CF_3CH=CHF$.

5. The process of claim 1 wherein the product mixture further comprises $CF_3CF=CH_2$; and wherein $CF_3CF=CH_2$ from the product mixture is recovered.

6. The process of claim 1 wherein the product mixture further comprises $CF_3CF_2CH_3$; and wherein a mixture of $CF_3CF_2CH_3$ and $CF_3CH=CHF$ is recovered and further reacted with HF in the liquid phase under fluorination conditions in the presence of a fluorination catalyst to produce a mixture comprising $CF_3CH_2CHF_2$ and $CF_3CF_2CH_3$.

7. The process of claim 1 wherein the product mixture further comprises $CF_3CF_2CH_3$; and wherein a mixture of $CF_3CF_2CH_3$ and $CF_3CH=CHF$ is recovered and further reacted under dehydrofluorination conditions in the presence of a dehydrofluorination catalyst to produce a mixture comprising $CF_3CH=CHF$ and $CF_3CF=CH_2$.

8. The process of claim 1 wherein the starting material is reacted in the vapor phase in the presence of a fluorination catalyst.

9. The process of claim 8 wherein the fluorination catalyst comprises at least one chromium-containing component selected from the group consisting of crystalline alpha-chromium oxide where from about 0.05 atom % to about 6 atom % of the chromium atoms in the alpha-chromium oxide lattice are replaced by trivalent cobalt atoms, and crystalline alpha-chromium oxide where from about 0.05 atom % to about 6 atom % of the chromium atoms in the alpha-chromium oxide lattice are replaced by trivalent cobalt atoms which has been treated with a fluorinating agent.

* * * * *